US009370410B2

(12) United States Patent
Yvoz

(10) Patent No.: US 9,370,410 B2
(45) Date of Patent: Jun. 21, 2016

(54) DEVICE FOR COLLECTION OF ANIMAL SEMEN ADAPTABLE TO AN ARTIFICIAL VAGINA

(75) Inventor: Jean-Francois Yvoz, Steenvoorde (FR)

(73) Assignee: IMV Technologies, L'Aigle (FR)

( * ) Notice: Subject to any disclaimer, the term of this patent is extended or adjusted under 35 U.S.C. 154(b) by 1668 days.

(21) Appl. No.: 11/921,525

(22) PCT Filed: Jun. 8, 2005

(86) PCT No.: PCT/IB2005/002314
§ 371 (c)(1),
(2), (4) Date: Apr. 1, 2008

(87) PCT Pub. No.: WO2006/131781
PCT Pub. Date: Dec. 14, 2006

(65) Prior Publication Data
US 2009/0137974 A1 May 28, 2009

(51) Int. Cl.
*A61D 19/00* (2006.01)
*A61D 19/02* (2006.01)
*A61M 1/00* (2006.01)

(52) U.S. Cl.
CPC ................ *A61D 19/021* (2013.01); *A61M 1/00* (2013.01)

(58) Field of Classification Search
CPC ......... A61D 19/00; A61D 19/02; A61M 1/00; A61F 5/44; A61F 5/00; A61K 9/22
USPC .......................................... 604/347, 327, 349
See application file for complete search history.

(56) References Cited

U.S. PATENT DOCUMENTS

| | | | | |
|---|---|---|---|---|
| 4,690,678 | A | 9/1987 | Douglas-Hamilton et al. | |
| 5,590,581 | A * | 1/1997 | Strub et al. | 99/302 R |
| 5,961,503 | A | 10/1999 | Simmet et al. | |
| 6,189,438 | B1 * | 2/2001 | Bielfeldt et al. | 99/321 |
| 6,517,559 | B1 * | 2/2003 | O'Connell | 606/158 |
| 6,652,496 | B2 * | 11/2003 | Bateman | 604/342 |
| 7,156,098 | B2 * | 1/2007 | Dolezal et al. | 128/206.11 |
| 2006/0234210 | A1 * | 10/2006 | Kenan et al. | 435/5 |

* cited by examiner

*Primary Examiner* — Tatyana Zalukaeva
*Assistant Examiner* — Ilya Treyger
(74) *Attorney, Agent, or Firm* — Harness, Dickey & Pierce, PLC

(57) ABSTRACT

The device (1) for collection of animal semen comprises a rigid (2) which is adaptable to an artificial vagina (V), and to which filtration means (3) and a collection receptacle (4) are fixed, the filtration means (3) being positioned inside the collection receptacle (4). The filtration means form a filtration pouch, preferably conical, that make it possible to hold back the "tapioca" and to allow the liquid fractions of the semen, including the "rich fraction" containing the spermatozoa, to pass into the collection receptacle (4).

34 Claims, 4 Drawing Sheets

DEVICE FOR COLLECTION OF ANIMAL SEMEN ADAPTABLE TO AN ARTIFICIAL VAGINA

TECHNICAL FIELD

This invention relates to the collection of animal semen. It has for object a novel device for collection of animal semen, which is adaptable to an artificial vagina and which makes possible a filtration of the animal semen collected. This collection device is preferably for single usage.

PRIOR ART

To take a sample of the semen of an animal, such as for example a boar, bull, stallion, rabbit, etc., it is at present customary to use artificial vaginas that make it possible to stimulate the penis of the animal and cause its ejaculation.

At present, there are numerous variants of artificial vaginas, whose structures are more or less complex, and which are generally adapted to the animal species from which a semen sample is desired.

For example, in the European Patent Application EP 0 699 422, a single-use artificial vagina of very simple structure is proposed, made of a non-toxic foam tube of polyurethane, polyethylene or silicone.

More sophisticated artificial vaginas are also known that make possible an automated stimulation of the penis, in particular by means of a variable pressure chamber fed by a fluid such as water or air.

For example, the International Patent Application WO 02/13723 discloses an artificial vagina implementing an air-tight air chamber and making possible a localized stimulation of the penis of the animal by means of pulsations.

The French patent FR 946 822 describes another known variant of embodiment of an artificial vagina for the collection of animal semen implementing a pressure chamber filled with water or air.

Whatever the structure of the artificial vagina used for the collection of the animal semen, it is necessary to associate with this artificial vagina a collection system into which the semen flows, as it exits the artificial vagina.

In the European Patent Application EP 0 699 422 cited above, this collection system is for example (FIG. 1) a cylindrical tube which is fitted into the tubular end of the foam artificial vagina. This collection tube comprises more particularly a cylindrical part that is closed, opposite the artificial vagina, by a conical part into which the sampled semen flows. In another form of embodiment (FIG. 2), the collection system is in two parts: a cylindrical tube open at both ends and fitted to the outlet of the artificial vagina; a separate receptacle.

In the French patent FR 946 822 cited above, the collection system is a rigid receptacle inserted in the end of the tube of the artificial vagina and held in position by ligatures.

Animal semen essentially comprises two different substances: a liquid substance and a substance forming a sort of gel and commonly designated "tapioca". The liquid substance essentially comprises three liquid fractions: a first liquid fraction is essentially made up of urine containing bacteria; a second liquid fraction, also commonly designated as the "rich fraction" is a creamy liquid containing spermatozoa; a third liquid fraction is the so-called "seminal fluid" which nourishes spermatozoa of the rich fraction. The so-called rich fraction is the fraction useful for the artificial insemination after the collecting step. The "tapioca" is in return useless for insemination. It is therefore necessary to separate the "tapioca" from the liquid fractions of the semen.

In a variant of embodiment (FIG. 2) of the French patent FR 946 822 cited above, it is proposed to carry out this separation by providing a discharge orifice for the "tapioca" in the tube interposed between the artificial vagina and the receptacle for seminal fluid. In the International Patent Application WO 02/13723, the suggestion is made to interpose a filter between the outlet of the artificial vagina and the receptacle (of goblet type) for the seminal fluid.

OBJECTIVES OF THE INVENTION

This invention has the principal objective of proposing a novel device for the collection of animal semen, which is adaptable to an artificial collection vagina, and which makes it possible to filter the animal semen.

An auxiliary objective of the invention is to propose a device for the collection of animal semen, which makes it possible to avoid any risk of contact of the animal semen, and in particular of the liquid fractions, with an outside element, and in particular with the operator handling the collecting and/or with the animal and/or with the surrounding air that might be polluted, thus improving the hygiene conditions of the collecting operation.

Another auxiliary objective of the invention is to propose a device for collection of animal semen, with an improved filtration of the animal semen avoiding the risk of clogging of the filtration medium by the "tapioca".

Another auxiliary objective of the invention is to propose a single-use device for collection of animal semen.

SUMMARY OF THE INVENTION

All or part of the above-mentioned objectives are attained by the collection device that is the subject of the appended claims.

The device for collection of animal semen of the invention principally comprises a frame that is adaptable to an artificial vagina and to which are fixed means for filtration and a collection receptacle, the means of filtration being positioned inside the collection receptacle.

Thus, the frame of the device of the invention fulfils a double function: it makes it possible to easily and rapidly adapt the device to the outlet of an artificial vagina; it serves as a common support for the means of filtration and for the collection receptacle.

The invention has for object both an artificial vagina and a device for collection of animal semen, the collection device being adaptable, preferably in a removable way, to the artificial vagina.

BRIEF DESCRIPTION OF THE FIGURES

Other characteristics and advantages of the invention will appear more clearly upon reading of the following detailed description of a preferred variant of embodiment of the invention, which description is given by way of non-restrictive and non-exhaustive example of the invention, and in reference to the appended drawings in which.

DETAILED DESCRIPTION

Figure 1:
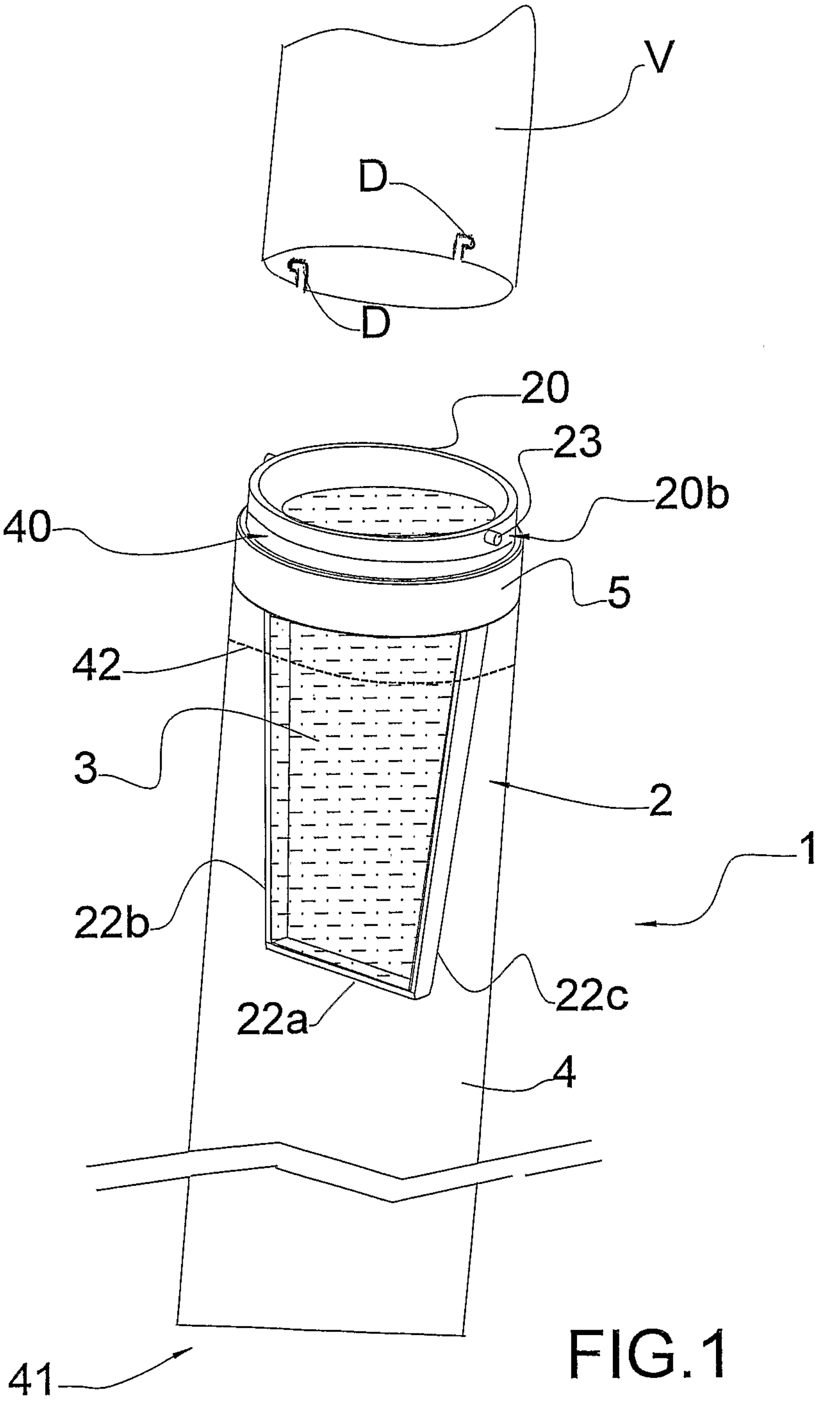
FIG. 1 is a perspective depiction of a collection device designed in accordance with a preferred variant of embodiment of the invention, and of the tubular end (outlet) of an artificial collection vagina designed to be assembled with said collection device.
Figure 7:
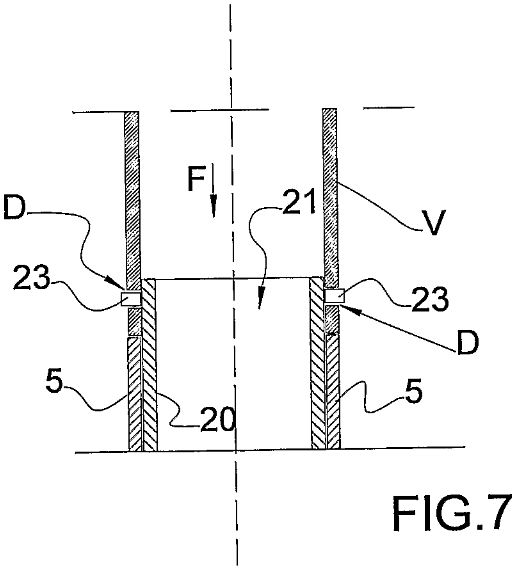
FIG. 7 is a longitudinal section view of the collection device and of the artificial vagina of FIG. 1, when they are assembled.

In FIG. 1 there is a depiction of a preferred variant of embodiment of a device 1 for the collection of animal semen, which is for a single use and which is adaptable to an artificial collection vagina V, so as to recover the animal semen as it comes out of this vagina. FIG. 7 depicts schematically the collection device 1 assembled with the artificial vagina V. In FIGS. 1 and 7, the vagina V was depicted in a very schematic way by a tubular element, knowing that the structure of this vagina V is without importance for the invention. The invention can in fact be implemented with any type of artificial collection vagina that makes it possible to stimulate the penis of an animal (in particular, boar, bull, stallion, rabbit, etc.). For example, the collection device 1 can be designed to be adapted to a single-use manual artificial vagina of very simple structure of the type described for example in the French patent FR 946 822. The collection device 1 can also be designed to be adapted to a more sophisticated artificial vagina of the type described for example in the International Patent Application WO 02/13723.

Referring to FIG. 1, the collection device 1 comprises a rigid frame 2, means of filtration 3, a receptacle 4, and a fixation ring 5.

Figure 2:
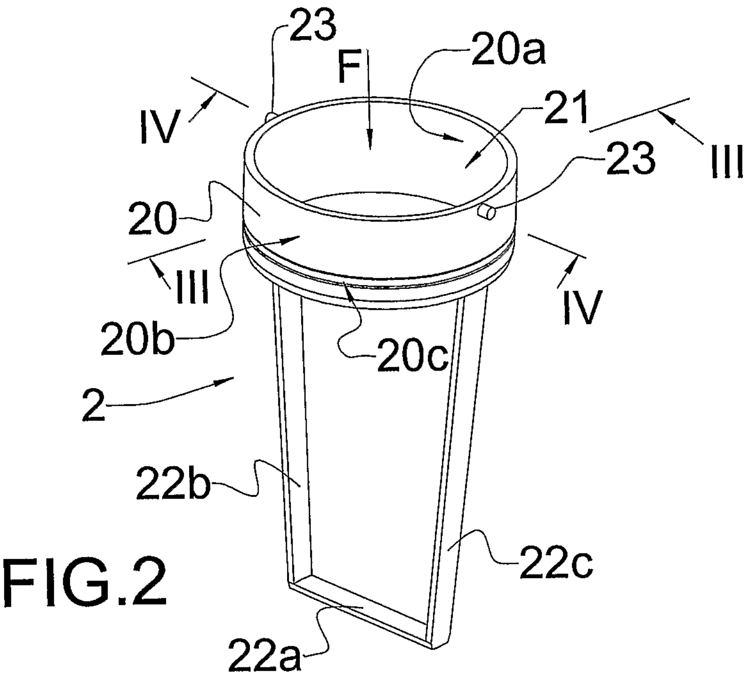
FIG. 2 is a perspective depiction of the part constituting the frame of the collection device of FIG. 1.

Referring to FIG. 2, the rigid frame 2 is made up of an adaptation ring 20 delimiting an inner passage 21 for the flow of the animal semen (arrow F) from the artificial vagina, and of an armature 22 that is approximately U-shaped, which extends in the direction of the flow of semen. Referring to FIG. 7, once the adaptation ring 20 is mounted to the outlet of the artificial vagina V, the inner passage 21 communicates with and extends the inner cavity of the artificial vagina V.

The geometry of the adaptation ring 20 is determined as a function of the geometry of the outlet of the artificial collection vagina V to which the collection device 1 is to be mounted. Under the circumstances, the outlet of the vagina V being cylindrical, the ring 20 presents a circular section. The invention is not, however, limited to the implementation of a ring with circular section, said ring can be replaced by any adaptation part delimiting a passage for the flow of the semen and presenting a geometry adapted to the outlet of the artificial collection vagina to which the collection device of the invention is to be mounted.

In the example of embodiment of the figures, the adaptation ring 20 comprises, on the outer wall 20*b*, two diametrically opposed assembly catches 23. Referring to FIG. 1, these assemblage catches 23 are designed to respectively work together with the cut-outs D contrived in the artificial vagina V, so as to make possible rapid bayonet-type assembly. The invention is not limited to this particular structure of rapid assembly means, the catches 23 and cut-outs D can be replaced by any known type of rapid assembly means that make possible a blockage of the translation of the ring 20 with respect to the vagina V. For example, in another variant of embodiment, the assembly of the ring 20 with the artificial vagina V could be obtained by a simple fitting together with tightening.

More preferably, the frame 2 (adaptation ring 20/armature 22/catches 23) is a one-piece part, for example made of plastic.

Figure 3:
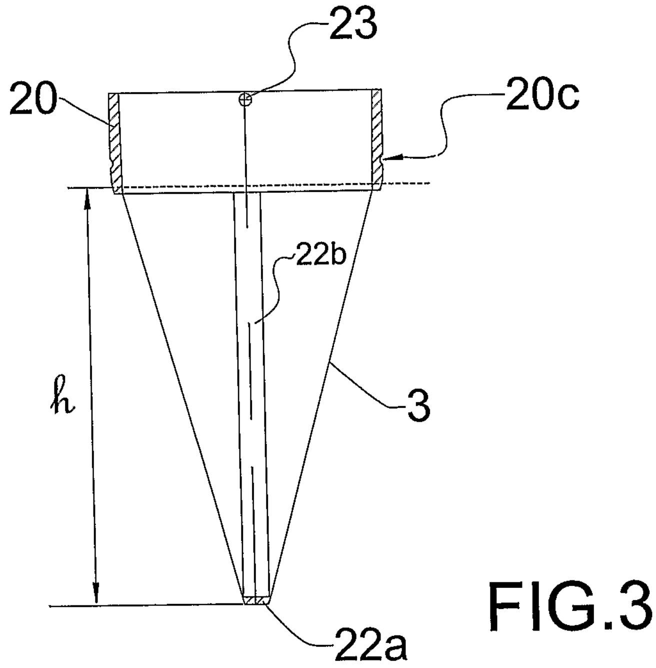
FIG. 3 is a longitudinal section view in the plane III-III of the frame of FIG. 2.

Referring to FIG. 3, the filtration means 3 are made up of a filtration medium made of textile, and more particularly by non-woven fabric, forming a filtration pouch. The function of these filtration means 3 is to block "tapioca" inside the filtration pouch, and to let the liquid fractions of the semen, including the "rich fraction" containing the spermatozoa, pass into the collection receptacle 4. The type of fibres constituting the non-woven fabric is without importance for the invention. The fibres of the non-woven filtration fabric 3 can for example be synthetic fibres made of polypropylene, polyethylene, etc., and/or natural cotton fibres, and/or artificial fibres of the viscous type. The use of a non-woven fabric to effect the filtration makes it possible to best advantage to manufacture a single-use filter. The invention is, however, not limited to the implementation of a non-woven fabric. The non-woven filtration fabric 3 can be replaced by any equivalent filtration means that make it possible to separate the tapioca from the rest of the animal semen.

More particularly, the non-woven filtration fabric 3 is fixed to the frame 2, for example by being glued and/or joined over the entire periphery of the interior wall 20*a* of the adaptation ring 20, and by being glued and/or joined to the arms 22*a*, 22*b* and 22*c* of the U-shaped armature 22. More preferably, to simplify manufacturing, the non-woven fabric 3 is formed of two identical parts 30, 31 symmetrical to each other. The frame 2 makes it possible to best advantage to form, with the non-woven filtration fabric 3, a filtration cone (FIG. 3). This filtration cone comprises an opening for the entry of semen of circular section corresponding to the inner section of the adaptation ring 20.

The armature 22 makes it possible to best advantage to maintain the shape of the filtration pouch 3 over its entire height h.

Figure 4:
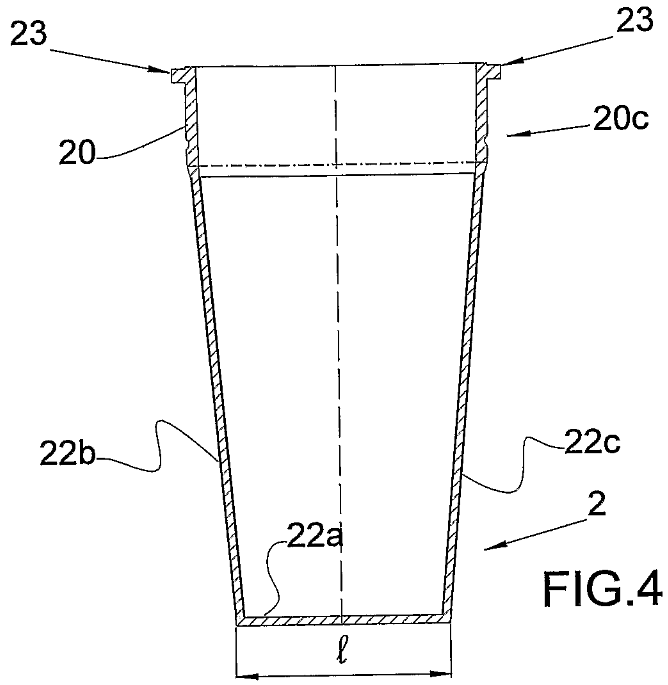
FIG. 4 is a longitudinal section view in the plane IV-IV of the frame of FIG. 2.

More preferably, referring to FIG. 4, the length (l) of the arm 22*a* forming the base of the U of the armature 22 is slightly less than the inner diameter of the adaptation ring 20, and the two diametrically opposed lateral arms 22*b* and 22*c* of the armature 22 are slightly divergent with respect to each other in the direction of the adaptation ring 20, which makes it possible to confer on the filtration pouch 3 the shape of a funnel (cone). The invention is, however, not limited to a U-shaped armature with divergent lateral arms, but can be replaced by any type of armature that makes it possible to maintain the shape of the filtration pouch over its entire height. In particular and non-exhaustively, in another variant of embodiment, the two lateral arms 22*b* and 22*c* of armature 22 can be approximately parallel.

Receptacle 4 is to best advantage a single-use flexible collection pouch, for example made of plastic. Referring to FIG. 1, this collection pouch 4 has a tubular shape, is open at one end 40 and closed at the opposite end 41. This collection pouch 4 is slipped onto the adaptation ring 20 by being fixed to the outer wall 20*b* of this ring 20. The filtration pouch 3 is thus seated inside the collection pouch 4, the two pouches 3 and 4 not being fixed to each other.

More particularly, in the preferred example of embodiment illustrated in the appended figures, fixation of the collection pouch 4 to the adaptation ring 20 is effected by means of the fixation ring 5, which is slipped onto and fixed to the adaptation ring 20, the collection pouch 4 being slipped on and wedged between the two rings 20 and 5.

Figure 5:
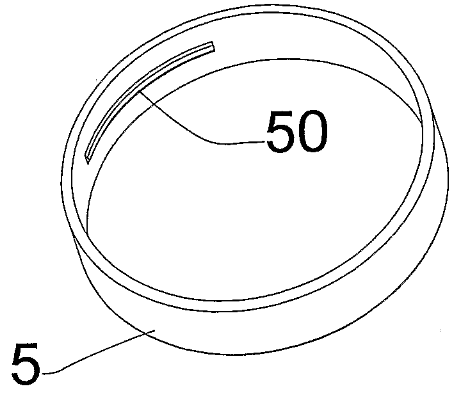
FIG. 5 is a perspective depiction of the fixation ring of the collection device of FIG. 1.
Figure 6:
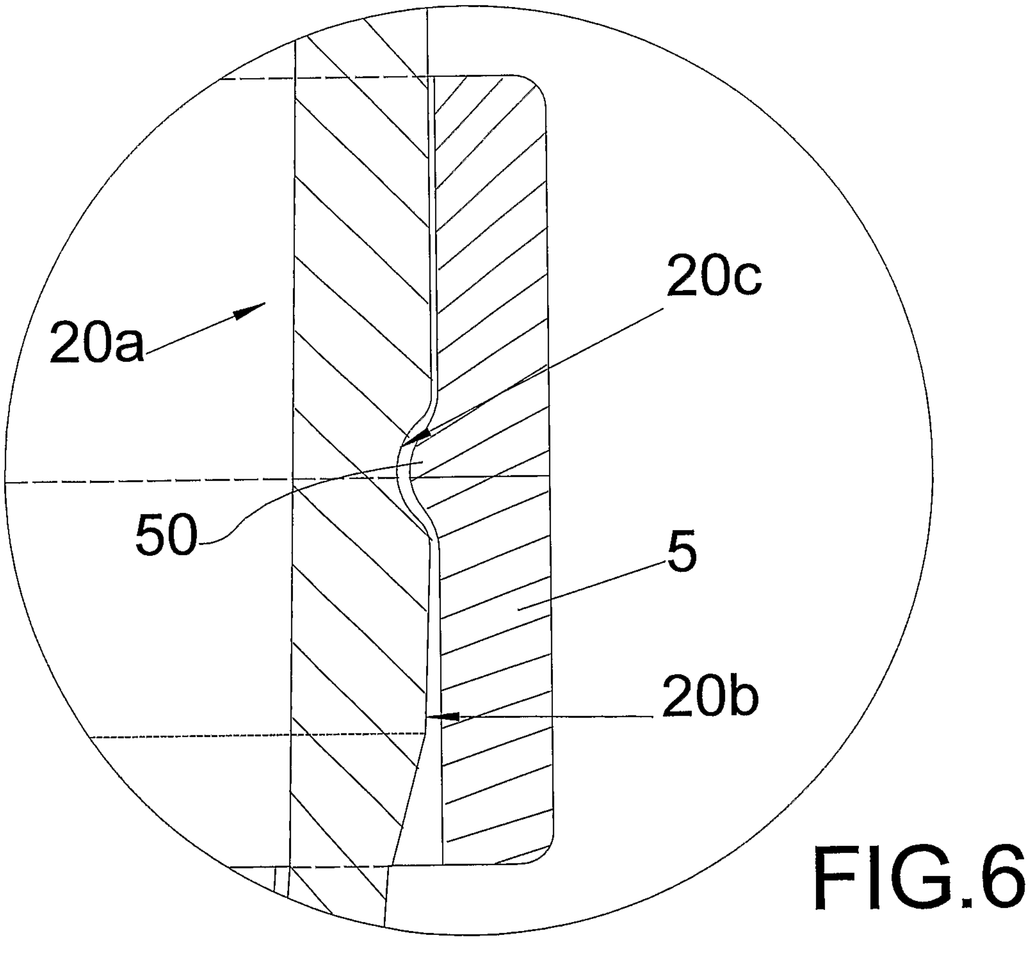
FIG. 6 is a detail of a cross-section view of the fixation ring of FIG. 5 and of the adaptation ring of the device of FIG. 1.

More particularly, referring to FIGS. 2, 5 and 6, the fixation ring 5 comprises two diametrically opposed internal lugs 50 that work together with a peripheral groove 20*c* contrived in the outer wall 20*b* of the adaptation ring 20, so as to make possible the blocking in position of the fixation ring 5 with respect to the adaptation ring 20. In FIG. 5, only one of the two lugs 50 is visible, the other, opposing, lug being masked.

Manufacture of the collection device is done in the following way. The filtration cone of FIG. 3 is manufactured (assembly of the non-woven filtration fabric 3 to frame 2). Next, the collection pouch 4 is positioned by slipping it onto the adaptation ring 20 of frame 2 of this filtration cone. Then, the fixation ring 5 is put in place by slipping and fitting it onto the adaptation ring 20 in such a way that the lugs 50 are positioned inside the groove 20*c* of the ring 20. The collection pouch 4 is immobilized by being wedged between the two rings 20 and 5. It should be noted that, for the sake of simplification, the collection pouch 4 is not depicted in FIG. 6.

The lugs 50 and the groove 20*c* could be replaced by any equivalent means that make it possible to hermetically fix the collection pouch 4 to the adaptation ring 20. For example, and non-exhaustively, in another variant of embodiment of the invention, the fixation ring 5 could be eliminated and replaced by gluing and/or heat-sealing the collection pouch 4 to the adaptation ring 20.

More preferably, the collection pouch 4 comprises a peripheral pre-cutout line 42 (FIG. 1), positioned in proximity to the adaptation ring 20, and that makes it possible to easily separate the collection pouch 4 into two parts, once the animal semen has been collected.

The collection device 1 of the invention, of which a preferred variant of embodiment was described with reference to the appended figures, is used in the following way.

Prior to the operation of collection of animal semen, the collection device 1 is assembled to the artificial collection vagina V. The artificial vagina V is slipped onto the penis of the animal (boar, bull, rabbit, etc.), and the customary operation of sampling of the animal semen is carried out, by stimulating the penis of the animal in a self-evident way by means of this artificial vagina V. According to the type of artificial vagina, the stimulation may be manual or automatic (pressure chamber fed by a fluid).

When the animal has expelled its semen by ejaculation, the latter flows into the inside of the filtration cone (2, 3) of the collection device of the invention. Once ejaculation of the animal semen is finished, the artificial vagina V equipped with collection device 1 is withdrawn, and, if need be, all of the animal semen is allowed to flow by gravity into the filtration cone (2, 3) of collection device 1. The non-woven fabric filter 3 of the filtration cone blocks the "tapioca" and allows the liquid fractions of the semen, including the "rich fraction" containing reproductive spermatozoa, to pass. Said liquid fractions flow by gravity into the collection pouch 4 by passing through the non-woven fabric filter.

More particularly, the non-woven filtration fabric 3 being held in shape by frame 2, the "tapioca" falls and accumulates to best advantage in the bottom of the non-woven fabric filter 3 (i.e., in the region of arm 22*a* of frame 2) without clogging the filter. This accumulation of "tapioca" in the bottom of the non-woven fabric filter 3 does not create an obstacle to the passage of the liquid fractions of the semen through the non-woven fabric wall of the filter. Thus, compared for example to a technical solution in which a filtration pouch made of non-woven fabric or its equivalent is fixed to the inside of a flexible collection pouch without being held in shape, filtration is improved by avoiding the risk of formation of clogs by the "tapioca".

Once the totality of the liquid fractions of the semen has passed through the non-woven fabric filter 3, the collection pouch 4 is manually cut out, following the pre-cutout line 42, so as to detach the part of pouch 4 containing the liquid fractions and located below the pre-cutout line 42. The operation of collection of the liquid fractions (including the "rich fraction") of the semen is then finished. To best advantage, all these collection operations are performed under optimal hygiene conditions by avoiding any risk of contact of the animal semen with an element exterior to the artificial vagina and the collection device, and in particular with the operator who is performing the collection, and/or with the animal, and/or with the surrounding air that might be polluted.

When the collection device 1 of the invention is removable with respect to the artificial vagina, such as in the examples illustrated in FIG. 1, once the above-mentioned collection operations have been performed, the collection device 1 containing the "tapioca" is withdrawn and it is discarded when this device is for single use.

It is important that the collection device 1 of the invention be removable with respect to the artificial vagina, when said vagina is not for single use and is to be reused, and/or when it is desirable to recover the collection device 1 for a new use. In the other cases (single-use collection device and single-use artificial collection vagina), it is not necessary that the collection device 1 be removable with respect to the artificial vagina V.

The invention is not limited to the preferred variant of embodiment which has just been described in a detailed way with reference to the appended figures, but extends to any other variant of embodiment covered by the appended claims.

The invention claimed is:

1. A device for filtration of animal semen received from an artificial vagina using a filter, the device adapted for collection of the animal semen in a collection pouch, the filter having a height defined from a closed first end to an open second end, the device comprising:

a rigid frame that comprises:

an adaptation ring with a coupling member operable for fixedly attaching the rigid frame to the artificial vagina; and an armature that extends from the adaptation ring, the armature includes a first lateral arm, a second lateral arm opposed to the first lateral arm, and a base arm extending from the first lateral arm to the second lateral arm, and wherein the filter is fixedly attached at least to the base lateral arm;

wherein the filter is fixedly attached at least to the armature such that the shape of the filter is maintained over an entirety of the height of the filter, and wherein the rigid frame is operable to fixedly attach the collection pouch such that the filter is positioned inside the collection pouch, wherein the collection pouch includes a peripheral pre-cutout line positioned in proximity to the adaptation ring, configured for separation of the collection pouch into two parts.

2. The device according to claim 1, wherein the coupling member includes a bayonet coupling member for fixedly attaching the rigid frame to the artificial vagina.

3. The device according to claim 1, wherein the filter is made of a textile material.

4. The device according to claim 3, wherein the filter is made of a non-woven fabric.

5. The device according to claim 1, wherein the adaptation part delimits a passage for the flow of animal semen, and the armature extends from the adaptation part in the direction of flow of the semen, wherein an inner wall of the adaptation part and the armature are each operable to cooperatively connect to and support the open second end of the filter, an outer wall of the adaptation part operable to fixedly attach to the collection receptacle such that the rigid frame is received within the collection receptacle.

6. The device according to claim 1, wherein the adaptation part and the armature are made up of the same one-piece part.

7. The device according to claim 1, wherein the armature presents a U-shape.

8. The device according to claim 5, further comprising an outer fixation ring, which receives and couples to the adaptation part to fix the collection receptacle in position between the fixation ring and the adaptation part.

9. The device according to claim 8, wherein the fixation ring is fitted and tightened onto the adaptation part of the frame.

10. The device according to claim 8, wherein the frame and the fixation ring are made of plastic.

11. The device according to claim 1, wherein the device is for single use.

12. An assembly adapted for the collection and filtration of animal semen comprising:

an artificial vagina that receives the animal semen:

a collection pouch that collects the animal semen;

a filter that filters the animal semen, the filter having a height defined from a closed first end to an open second end, the open second end operable to receive the animal semen from the artificial vagina; and a rigid frame that is received within the collection pouch that includes:

an adaptation ring operable for attaching to the artificial vagina; and an armature that extends from the adaptation ring, the armature includes a first lateral arm, a second lateral arm opposed to the first lateral arm, and a base arm extending from the first lateral arm to the second lateral arm, and wherein the filter is fixedly attached at least to the base lateral arm;

wherein the filter is fixedly attached at least to the armature such that the shape of the filter is maintained over an entirety of the height of the filter, and wherein the rigid frame is operable to fixedly attach the collection pouch such that the filter is received within the collection pouch, wherein the collection pouch comprises a peripheral prc-cutout line positioned in the proximity to the adaptation ring, configured for separation of the collection pouch into two parts.

13. The assembly of claim 12, wherein the filter is a conical pouch.

14. The assembly of claim 12, wherein the collection receptacle is a flexible pouch that has a single open end.

15. The assembly of claim 14, wherein the flexible pouch has a frangible portion operable for separating the flexible pouch into two parts.

16. The assembly of claim 12, wherein the adaptation part includes a coupling member operable for fixedly attaching to the artificial vagina.

17. The assembly of claim 16, wherein the coupling member includes a bayonet coupling member for fixedly attaching the frame to the artificial vagina.

18. The assembly of claim 12, further comprising an outer fixation ring, which receives and couples to the adaptation part to fix the collection receptacle in position between the fixation ring and the adaptation part.

19. The assembly of claim 12, wherein the armature includes a plurality of arms arranged in a U-shape that extends from the adaptation part.

20. The assembly of claim 12, wherein the adaptation part delimits a passage for the flow of the animal semen, and the armature extends from the adaptation part in the direction of flow of the animal semen, wherein an inner wall of the adaptation part and the armature are each operable to cooperatively connect to and support the open second end of the filter, an outer wall of the adaptation part operable to fixedly attach to the collection receptacle such that the rigid frame is received within the collection receptacle.

21. The assembly of claim 12, wherein the filter is also fixedly attached to the adaptation part of the rigid frame.

22. The assembly of claim 12, wherein the filter is glued to the rigid frame.

23. The device of claim 1, wherein the filter is also fixedly attached to the adaptation part of the rigid frame.

24. The device of claim 1, wherein the filter is glued to the rigid frame.

25. A device for filtration of animal semen received from an artificial vagina and for collection of the animal semen in a collection pouch, the device comprising a rigid frame that comprises:

an adaptation ring with a coupling member operable for fixedly attaching the rigid frame to the artificial vagina; and an armature for maintaining the shape of the filter, said armature extending from the adaptation ring, the armature includes a first lateral arm, a second lateral arm opposed to the first lateral arm, and a base arm extending from the first lateral arm to the second lateral arm, and wherein the filter is fixedly attached at least to the base lateral arm;

wherein the filter is fixedly attached at least to the armature, and the rigid frame is operable to fixedly attach the collection pouch such that the filter is received within the collection pouch, wherein the collection pouch includes a peripheral prc-cutout line positioned in the proximity to the adaptation ring, configured for separation of the collection pouch into two parts.

26. The device according to claim 25, wherein the filter is fixedly attached to at least the armature such that the shape of the filter is maintained over an entirety of the height of the filter.

27. The device according to claim 25, wherein the filter is also fixedly attached to the adaptation part of the rigid frame.

28. The device according to claim 25 wherein the filter is glued to the rigid frame.

29. The device according to claim 25, wherein the filter is made of a textile material.

30. The device according to claim 25, wherein the filter is made of a non-woven fabric.

31. The device according to claim 25, wherein the collection receptacle is a flexible pouch that has a single open end.

32. The device according to claim 31, wherein the flexible pouch has a frangible portion operable for separating the flexible pouch into two parts.

33. The device according to claim 25, wherein the armature presents a U-shape.

34. The device according to claim 25, wherein the adaptation part and the armature are made up of the same one-piece part.

* * * * *